United States Patent
Heintzenberg et al.

(10) Patent No.: US 6,766,702 B2
(45) Date of Patent: Jul. 27, 2004

(54) METHOD AND APPARATUS FOR INVESTIGATING TEMPORAL DEVELOPMENT OF PARTICLES OR DROPLETS IN GAS-VAPOR MIXTURE

(75) Inventors: Jost Heintzenberg, Leipzig (DE); Robert J. Charlson, Seattle, WA (US); Frank Stratmann, Leipzig (DE); Manfred Wendisch, Parthenstein (DE); Sabine Wurzler, Leipzig (DE)

(73) Assignee: Institute for Tropospheric Research, a German non-profit organization, Leipzig (DE)

( * ) Notice: Subject to any disclaimer, the term of this patent is extended or adjusted under 35 U.S.C. 154(b) by 158 days.

(21) Appl. No.: 09/907,071

(22) Filed: Jul. 16, 2001

(65) Prior Publication Data

US 2003/0020050 A1 Jan. 30, 2003

(51) Int. Cl.[7] ................................................ G01N 15/02
(52) U.S. Cl. .................... 73/865.5; 73/1.06; 73/1.03; 73/865.5; 702/29
(58) Field of Search ................................ 73/1.06, 1.03, 73/865.5; 702/29

(56) References Cited

U.S. PATENT DOCUMENTS 4,710,887 A * 12/1987 Ho .......................... 73/863.22

OTHER PUBLICATIONS

Bartlett, B.M. and G.P. Ayers, "Static Diffusion Cloud Chamber," *J. Rech. Atmos.* 15(3–4):231–233, 1981.

Cziczo, D.J. and J.P.D. Abbatt, "Deliquescence, Efflorescence, and Supercooling of Ammonium Sulfate Aerosols at Low Temperature: Implications for Cirrus Cloud Formation and Aerosol Phase in the Atmosphere," *Journal of Geophysical Research* 104(D11):13,781–13,790, 1999.

Elliott, W.P., "Dimensions of Thermal Diffusion Chambers," *Journal of the Atmospheric Sciences*, Jul. 1971, pp. 810–811.

Garnier, J.P. et al., "Water Droplet Growth Study in a Continuous Flow Diffusion Cloud Chamber," *Atmospheric Research* 21:41–51, 1987.

Hoppel, W.A. et al., "A Cloud Chamber Study of the Effect That Nonprecipitating Water Clouds Have on the Aerosol Size Distribution," *Aerosol Science and Technology* 20:1–30, 1994.

Hudson, J.G. and Patrick Squires, "An Improved Continuous Flow Diffusion Cloud Chamber," *Journal of Applied Meteorology*, Jul. 1976, pp. 776–782.

Lala, G.G. and J.E. Jiusto, "An Automatic Light Scattering CCN Counter," *Journal of Applied Meteorology*, Apr. 1977, pp. 413–418.

(List continued on next page.)

*Primary Examiner*—Hezron Williams
*Assistant Examiner*—André K. Jackson
(74) *Attorney, Agent, or Firm*—Christensen O'Connor Johnson Kindness PLLC

(57) ABSTRACT

The present invention relates to a method for investigating the behavior of particles or droplets in a gas-vapor mixture inside a flow device, which is useful for studying cloud dynamical and microphysical processes. The invention allows adjustment and/or control of the thermodynamic system parameters based on the observed behavior of an internal standard with known properties, thus achieving a well-defined vapor concentration and saturation field inside the flow device. By injecting particles or droplets to be investigated into this well defined flow device, and measuring the size of the particles or droplets, the activation and growth or shrinking behavior of the particles or droplets may be determined using a mathematical model of the fluid, thermodynamic, and chemical conditions of the flow device.

24 Claims, 5 Drawing Sheets

OTHER PUBLICATIONS

Mallant, R.K.A.M., "A Fog Chamber and Wind Tunnel Facility for Calibration of Cloud Water Collectors," in M.H. Unsworth et al. (eds.), *Acid Deposition at High Elevation Sites*, Kluwer Academic Publishers, Dordrecht, Boston and London, pp. 478–490.

Nenes, A. et al., "A Theoretical Analysis of Cloud Condensation Nucleus (CCN) Instruments," *Journal of Geophysical Research 106*( D4):3449–3474, 2001.

Saxena, V.K. et al., "Operation of the Thermal Diffusion Chamber for Measurements on Cloud Condensation Nuclei," *Journal of the Atmospheric Sciences 27*:73–80, Jan. 1970.

Wagner, P., "Optical Determination of the Size of Fast-Growing Water Droplets in an Expansion Cloud Chamber," *Journal of Colloid and Interface Science 44*(1):181–183, 1973.

* cited by examiner

METHOD AND APPARATUS FOR INVESTIGATING TEMPORAL DEVELOPMENT OF PARTICLES OR DROPLETS IN GAS-VAPOR MIXTURE

FIELD OF THE INVENTION

The present invention relates to a method for investigating the behavior of particles or droplets in a gas-vapor mixture inside a flow device, which can be used to study cloud droplet dynamic and microphysical processes.

BACKGROUND OF THE INVENTION

Atmospheric clouds are complicated systems. Many important processes in clouds are still not completely understood. For example, the activation of aerosol particles into drops, the effects of water vapor diffusion on the growth or shrinking of aerosol particles/drops, or the adsorption (or absorption) and desorption of trace gasses in moist aerosol particles (and the role trace gasses play in the growth or shrinking of aerosol particles/drops) are not completely understood.

In order to obtain a better understanding of the chemical and microphysical processes in clouds, many attempts have been made over the last century and in recent years to study clouds by means of field and laboratory experiments as well as numerical models. Some prior attempts and their corresponding devices can be found in Cziczo, D. J. and J. P. D. Abbatt, "Deliquescence, efflorescence, and supercooling of ammonium sulfate aerosols at low temperature: Implications for cirrus cloud formation and aerosol phase in the atmosphere," *J. Geophys. Res.*, 104(11):13781–13790 (1999); Chuang, P. Y.-S., 1999, "Experimental and theoretical studies of cloud condensation nuclei," Ph.D.-thesis, California Institute of Technology, Pasadena, Calif., p. 157; and Nenes et al., *J. Geophys. Res.*, 106:3449–3474 (2001).

Clouds exist in their natural environment—the atmosphere—which itself is a fairly complicated system. Therefore, it is not a trivial task to study or even produce realistic clouds in a laboratory. For example, all of the prior devices referenced above depend on measurements of one or a few water supersaturations, and then require theoretical modeling to predict, based on the measurements, what might happen in real clouds. Thus, in these devices, it is not possible to accurately simulate the time dependence of drop growth or shrinking as it occurs in the lower atmosphere (troposphere). Further, the prior devices are based on the assumption that above a certain supersaturation level aerosol particles are spontaneously activated into droplets. Thus, these prior devices do not consider, and thus not simulate, subsaturation conditions in which aerosol particles remain unactivated.

Still further, existing methods as used in the prior devices for studying the growth or shrinking of particles/droplets in a vapor field inside a flow tube or static chamber also have the disadvantage that their thermodynamic system parameters cannot be defined with sufficient accuracy. For example, these methods are substantially dependent on the accuracy of their temperature and vapor pressure control devices, which are unfortunately not capable of setting these parameters as accurately as one would desire. Usually, the vapor concentration and saturation field inside a flow tube or static chamber are determined with analytical or numerical models, which depend on the experimental data, such as temperature differences, as boundary conditions. Thus, uncertainties in the thermodynamic system parameter control devices, such as the temperature control device, negatively influence the model predictions. Typically, either thermoelectric elements or thermocouples are employed to control the temperature of either the wall of a flow tube or the temperature of a cooling liquid in a double jacket wrapped around a flow tube or static chamber. State of the art temperature control units manage to achieve an accuracy in the range of +/−0.1° K to 0.05° K. This still leads to uncertainties in the vapor field inside the flow tube or static chamber, with the consequence that the thermodynamic conditions under which particles/droplets are to grow cannot be adequately defined. As a result, there are large uncertainties as to the resulting sizes of the particles/droplets. For example, for water vapor, such temperature deviations (uncertainties) may even lead to a completely uncontrolled system, which may reach either supersaturated or subsaturated condition in the limits of the accuracy of the temperature control.

Also, in these prior devices, it is not possible to detect the influence of trace gasses upon the growth or shrinking of particles/droplets in a gas-vapor mixture.

A need exists for a method and apparatus that accurately simulate the time dependence of both subsaturation and supersaturation conditions in an atmospheric cloud, in order to permit the study of both unactivated and activated particles or droplets. Such method and apparatus would be suited for simulating the time dependence of drop growth or shrinking as it occurs in the lower atmosphere (troposphere). Preferably, such method and apparatus should allow for accurate control of thermodynamic system parameters so as to establish a well-defined vapor concentration and saturation field inside a flow device. Further preferably, such method and apparatus should permit observing the influence of trace gaseous species on droplet or particle growth or shrinking.

SUMMARY OF THE INVENTION

The present invention provides a method for investigating the behavior of particles or droplets (e.g., NaCl, soot, ammonium sulfate, sulfuric acid, biological particles such as pollen) in a gas-vapor mixture inside a flow device, which can meet all the needs described above.

The method generally includes five steps. First, a flow device is provided, including an internal standard with known properties and behavior therein. Specifically, particles or droplets with known and/or defined size, chemical composition, concentration (e.g., number concentration), and growth or shrinking behavior in a gas-vapor mixture are used as the internal standard, and included in or injected into the flow device.

Second, various thermodynamic system parameters of the flow device are adjusted based on the observed behavior of the internal standard. For example, the particle or droplet size profile (i.e., how various particle sizes are spatially distributed) and the concentration profile (i.e., how the concentration is spatially distributed) of the internal standard are determined by measurement using any suitable space and/or time resolved measurement methods, preferably optical methods, as well known in the art. Based on the measured behavior of the internal standard, the thermodynamic system parameters of the flow device are adjusted and/or controlled in such a way that a desired particle or droplet size profile of the internal standard is achieved. In other words, the parameters are adjusted so that the particles or droplets of the internal standard will grow as they should in accordance with their known activation and growth behavior. Thus, this adjustment of the thermodynamic system parameters, in turn, achieves a well-defined vapor concentration and saturation field inside the flow device.

Third, particles or droplets to be investigated are injected into this well defined flow device, either independently or with the internal standard.

Fourth, the actual particle or droplet size of the injected particles or droplets is measured. As before, this is accomplished by using any suitable space and/or time resolved measurement methods, preferably optical methods.

Fifth, the behavior, for example the activation and growth or shrinking behavior of the particles or droplets to be investigated, is determined based on the measured size of the particles or droplets and the adjusted system parameters, using a mathematical/numerical model.

Various applications or modifications of a method according to the present invention are possible. For example, in the third step, the particles or droplets to be investigated may be injected into the flow device together with trace gasses. In this case, the particles or droplets to be investigated are with known and/or defined size, chemical composition, concentration (e.g., number concentration), and growth or shrinking behavior. Thereafter, in the fourth step, as before, the particle or droplet size of the injected particles or droplets to be investigated is measured. In the fifth step, the behavior of the particles or droplets to be investigated is determined based on their measured size and the adjusted system parameters using a mathematical model. Specifically, in this case, any effects of the trace gasses on the activation and growth or shrinking behavior of the particles or droplets can be determined, by comparing the determined behavior against the predefined growth or shrinking behavior of the particles or droplets without the presence of trace gasses.

As another application example, in the third step, the particles or droplets to be investigated may be with known or predefined concentration (variable). In the fourth step, as before, the particle or droplet size of the injected particles or droplets is measured. Finally, in the fifth step, the behavior of the particles or droplets to be investigated is determined based on their measured size and the adjusted system parameters using a mathematical model. Specifically, in this case, any effects of the concentration (e.g., number concentration) of the particles or droplets on the activation and growth or shrinking behavior of the particles or droplets can be determined by repeating the method with each time varying the concentration of the particles or droplets.

According to one aspect of the present invention, the flow device suited for carrying out a method of the present invention is a flow tube, preferably a laminar flow tube.

A method of the present invention is particularly suited for simulating both subsaturation and supersaturation conditions in an atmospheric cloud, including both unactivated and activated particles or droplets, to permit a realistic study of cloud droplet dynamic and microphysical processes. According to the present invention, the thermodynamic system parameters of the flow device can be accurately controlled and defined so as to establish a well-defined vapor concentration and saturation field, thereby closely simulating the thermodynamic conditions of real atmospheric clouds. Furthermore, the invention permits injecting trace gasses into the flow device together with the particles or droplets to be investigated, thus allowing for the investigation of the role of, for example, organic compounds in the formation of clouds.

BRIEF DESCRIPTION OF THE DRAWINGS

The foregoing aspects and many of the attendant advantages of this invention will become more readily appreciated by reference to the following detailed description, when taken in conjunction with the accompanying drawings, wherein.

DETAILED DESCRIPTION OF THE PREFERRED EMBODIMENT

The present invention provides a method for investigating the behavior of particles or droplets (e.g., NaCl, soot, ammonium sulfate, sulfuric acid, biological particles such as pollen) in a gas-vapor mixture inside a flow device.

Figure 1:
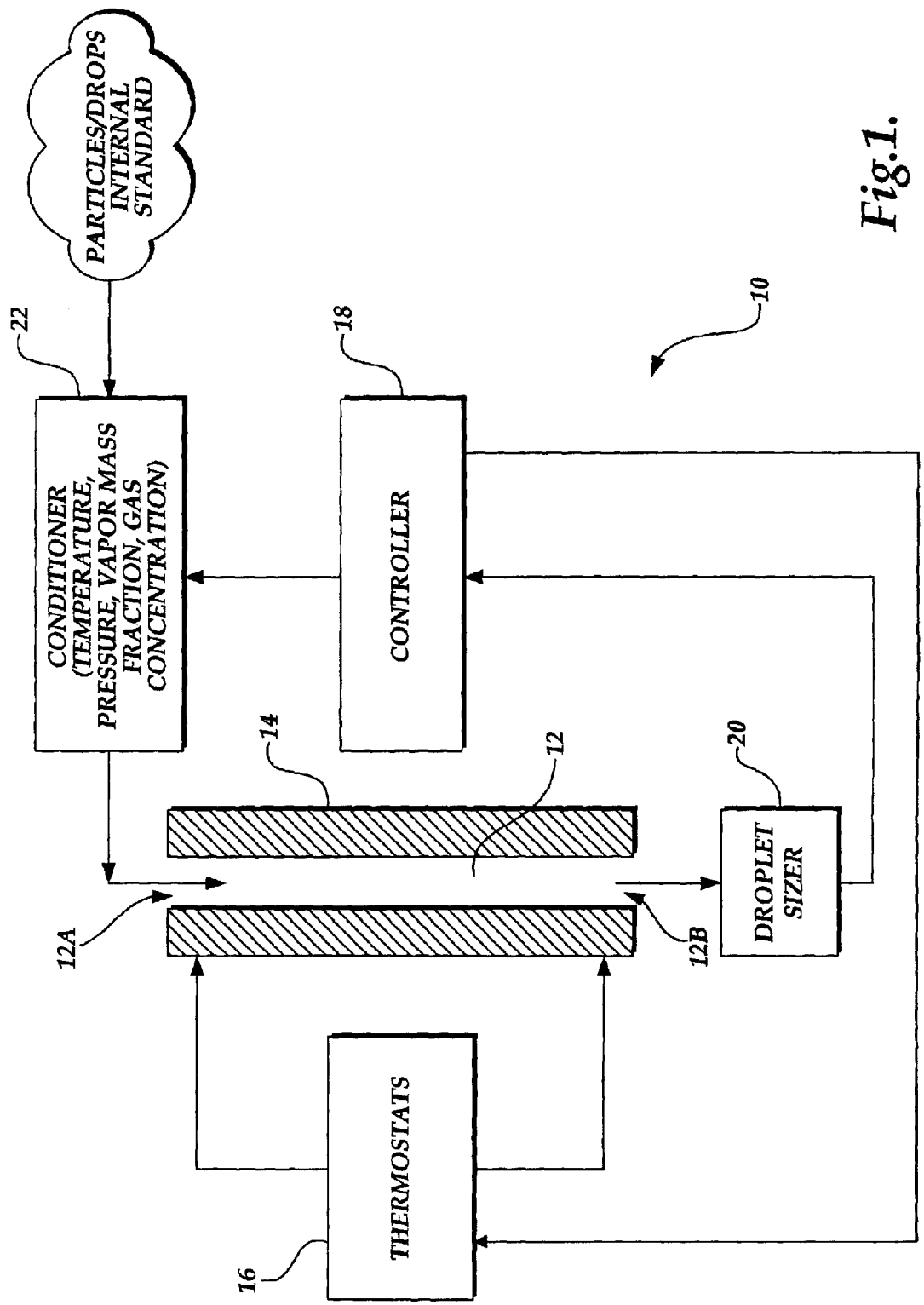
FIG. 1 is a schematic diagram of a flow tube constructed in accordance with the present invention, suitable for carrying out a method of the invention.

FIG. 1 schematically illustrates an apparatus suitable for carrying out a method of the present invention. An apparatus 10 includes a flow device 12, preferably a flow tube, further preferably a laminar flow tube. The flow device 12 is wrapped by thermostated double jacket 14, which is coupled to thermostats 16. The thermostats 16 measure changes in the temperature of the double jacket 14 and control sources of heating and cooling (not shown) to maintain a desired temperature. The desired temperature of the double jacket 14 to be maintained, in turn, is determined by a controller 18. The flow device 12 defines an inlet 12A and an outlet 12B, through which particles or droplets enter and exit the flow device 12, respectively. Adjacent to the outlet 12B, a particle/droplet sizer 20 is located, which may be any suitable time and/or space resolved droplet size measuring means, for example an optical measuring device, as well known in the art. The particle size information determined by the particle/droplet sizer 20 is relayed to the controller 18. Then, the controller 18, based on the particle size information received from the particle/droplet sizer 20, controls a conditioner, collectively identified with reference numeral 22, through which particles or droplets are conditioned prior to entering the flow device 12 via the inlet 12A. Specifically, the conditioner 22 may include means for controlling the temperature, pressure, vapor mass fraction, and gas concentration of the particles or droplets, as well known in the art. For each parameter to be controlled in the conditioner 22, a particle/droplet size measurement is needed. For example, when two temperatures are to be controlled, the particle/droplet size at, for example, two different locations need to be measured. Otherwise the system would be underdetermined.

Figure 2A:
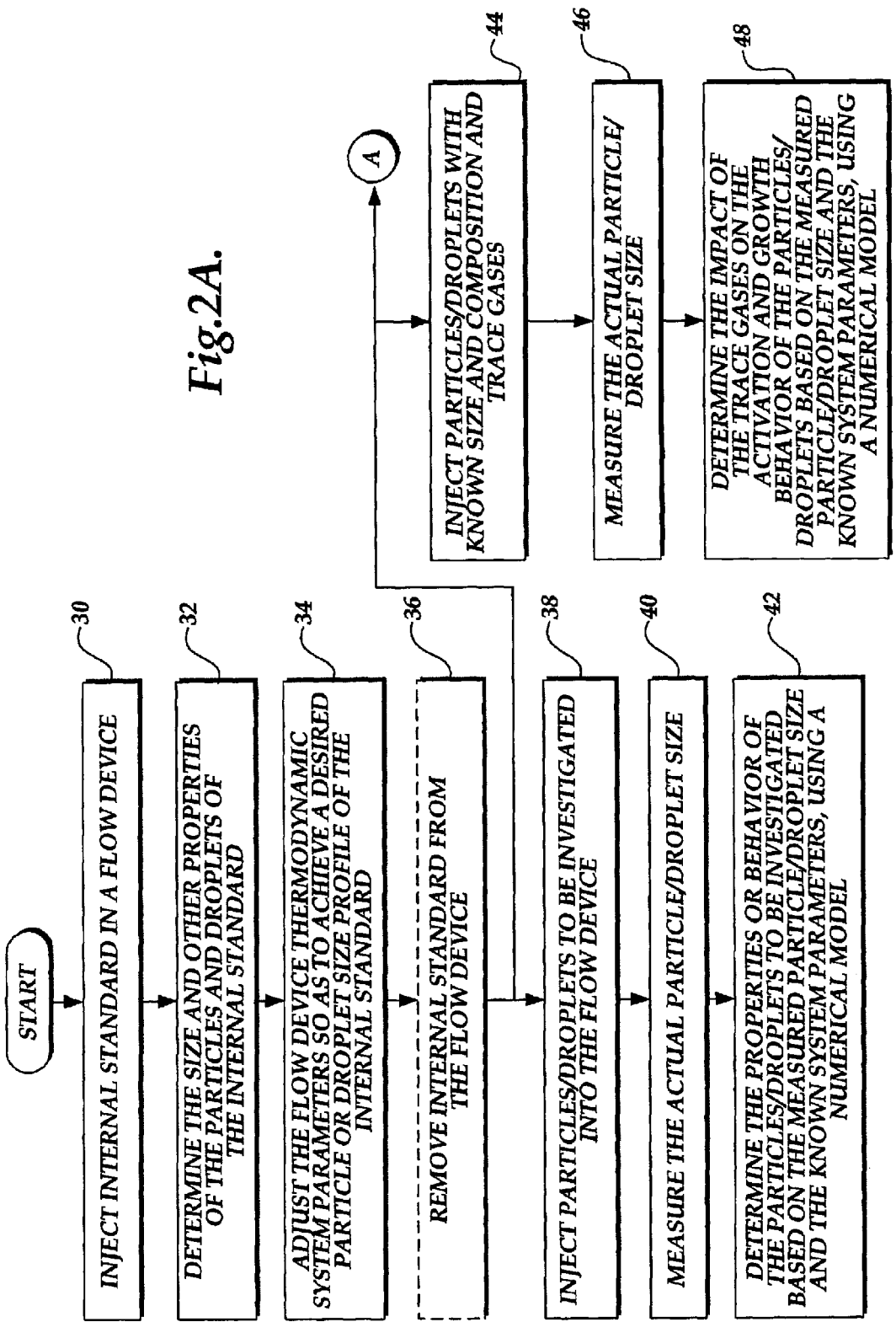
FIGS. 2A and 2B depict a flow chart illustrating steps included in methods for investigating the temporal development of particles or droplets in a gas-vapor mixture, according to the present invention.

Referring additionally to FIG. 2A, a method of the present invention carried out using the apparatus 10 illustrated in FIG. 1 is described. In step 30, first, an internal standard is injected into the flow device 12. The internal standard comprises particles or droplets with known and/or defined size, chemical composition (e.g., NaCl), concentration (e.g., number concentration), and growth or shrinking behavior in a gas-vapor mixture. In one embodiment, sub-micrometer-sized NaCl particles are used as the internal standard. In next step 32, after passage of a predetermined time, the particle or droplet size (preferably measured along the axis (length) of the flow device) profile and (if needed) the concentration (e.g., number concentration) profile of the internal standard are determined. These determinations are made using suitable space and/or time resolved measurement methods, for example optical methods, as well known in the art.

In step 34, the thermodynamic system parameters of the flow device 12, for example the boundary temperatures and/or the vapor content and/or the pressure, are adjusted by the controller 18, so as to achieve a desired particle or droplet size profile of the internal standard. In other words, the thermodynamic system parameters of the flow device 12 are adjusted to closely simulate the thermodynamic conditions of real atmospheric clouds, so as to reliably achieve the predefined particle or droplet size profile of the internal standard. In this regard, as a specific example, the controller 18 may be configured to determine a difference between a measured particle or droplet size and a desired particle or droplet size (as known based on the predefined growth or shrinking behavior of the internal standard), and then to control the thermodynamic system parameters so as to minimize the difference.

In step 36, the internal standard may be removed from the flow device 12. Then, in step 38, particles or droplets to be investigated are injected into the flow device 12. Alternatively, the internal standard need not be removed from the flow device 12 (skipping step 36), and thus the particles or droplets to be investigated may coexist with the internal standard in the flow device 12 in step 38. The particles or droplets to be investigated may be with known, determined, or unknown size, concentration (e.g., number concentration), chemical composition, and growth or shrinking behavior, in a gas-vapor mixture.

In step 40, the behavior of the particles or droplets to be investigated is observed by measuring their particle or droplet size, and (if needed) their concentration (e.g., number concentration), using any suitable space and/or time resolved measurement means, preferably optical means. In this regard, the number concentration of the particles or droplets, which have grown larger than a predetermined size and thus are "activated" to form drops, can be determined using conventional optical methods.

Finally, in step 42, based on the known (adjusted) thermodynamic system parameters, a mathematical/numerical model is used to determine the fluid, thermodynamic, and chemical conditions in the flow device 12. Based on the determined fluid, thermodynamic, and chemical conditions, models describing the particle behavior as a function of time and space (e.g., the activation behavior or the growth or shrinking behavior) can be constructed to predict the particle or droplet size and also, if desired, the concentration profile in the flow device 12.

A method of the present invention, generally described above, can be implemented for use in various applications. For example, the method including steps 30–42 as described above may be used to examine existing and/or new activation laws and growth laws. Specifically, after the thermodynamic system parameters (e.g., boundary temperatures, vapor content, etc.) are adjusted in step 34, in step 38, particles or droplets to be investigated of known and/or defined or unknown size with known or unknown chemical composition (e.g., particles from the atmosphere) with known and/or defined or unknown concentration (e.g., number concentration) are injected into the flow device 12. In one preferred embodiment, particles or droplets with known and/or determined size and composition and unknown growth or shrinking behavior are injected. In step 40, the actual particle or droplet size of the particles or droplets to be investigated is then measured using any suitable space and/or time resolved measurement method. In step 42, the actual temperature, vapor concentration, vapor saturation, and particle size profile are calculated based on the known system parameters, using a mathematical/numerical model and by adopting the boundary conditions for the vapor mass fraction, and finally, the particle/droplet growth or shrinking model is constructed and/or examined. For known vapor saturation profiles, the activation and growth or shrinking behavior of the particles or droplets can be determined.

As another example, the apparatus 10 used in the method generally described in steps 30–42 can be carried out as a cloud droplet simulator. In this case, after the thermodynamic system parameters are adjusted in step 34, in step 38, particles or droplets of unknown or known and/or determined size and known or unknown chemical composition and known and/or determined or unknown number concentration are injected into the flow device 12. In step 40, the actual particle or droplet size of the particles or droplets to be investigated is measured. In step 42, the actual temperature, vapor concentration, vapor saturation, and particle size profile are calculated based on the known system parameters, using a mathematical/numerical model and by adopting the boundary conditions for the vapor mass fraction, and finally, the particle/droplet growth or shrinking model is constructed and/or examined. For known fluid, thermodynamic, and chemical system parameter profiles (e.g., saturation profiles), the numbers of both activated and unactivated particles or droplets can be determined.

As yet another example, a method may be implemented to examine existing and/or new gas scavenging and growth laws related to the effects of trace gasses. In this embodiment, steps 30–36 are carried out as described above. Thereafter, referring to FIG. 2A, in step 44, particles or droplets with known size and composition are injected into the flow device 12 together with trace gasses, for example, $SO_2$, $NH_3$, or $HNO_3$. In a next step 46, the actual particle/droplets size of the particles or droplets to be investigated is measured using suitable means, such as conventional optical means. Finally, in step 48, the impact of trace gasses, if any, on the activation and growth or shrinking behavior of the particles or droplets to be investigated is determined, based on the measured particle/droplet size and the known system parameters, using a mathematical/numerical model. Specifically, the actual temperature, vapor concentration, vapor saturation, trace gas concentration, and particle size profile are calculated based on the known system parameters, using a mathematical/numerical model, and finally, models describing the gas scavenging and liquid phase processes are constructed and/or examined. For known fluid and thermodynamic system parameter profiles (e.g., saturation profile and trace gas concentration profile), the impacts of trace gasses on the activation and growth or shrinking behavior of the particles or droplets can be determined.

Figure 2B:
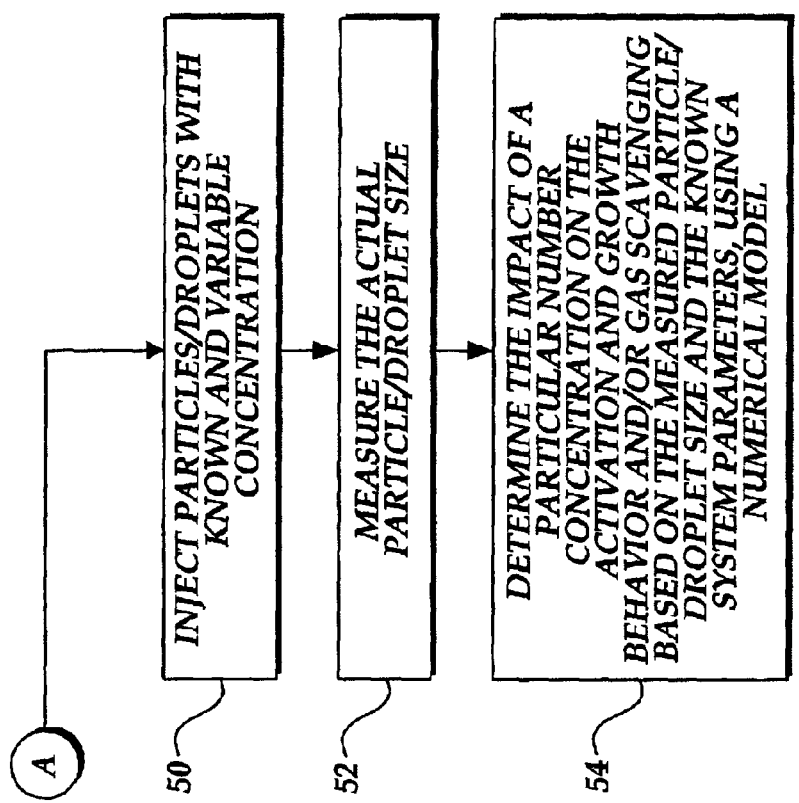

As a further example, a method may be implemented to investigate the effects of the particle number concentration on the activation and growth or shrinking behavior and/or the gas scavenging. Specifically, still referring to FIG. 2A and also FIG. 2B, after performing steps 30–36, in step 50, particles or droplets to be investigated with known (and variable) concentration (e.g., number concentration) are injected into the flow device 12. In a next step 52, the actual particle size of the particles or droplets to be investigated is measured using a conventional method, for example an optical method. In step 54, the impact of a particular number concentration on the activation and growth or shrinking behavior of the particles or droplets to be investigated is determined, based on the measured particle/droplet size and the known system parameters, using a mathematical/numerical model. Specifically, for known saturation profile and, where necessary, known trace gas concentration profile, conclusions can be drawn concerning the impact of the particle number concentration on the activation and growth or shrinking behavior and/or the gas scavenging.

As a still further example, according to a method of the present invention, the particle size or concentration measurement of the particles or droplets to be investigated may be repeatedly carried out by each time varying the system parameters, to ascertain the effects of varying system parameters on the activation and growth or shrinking behavior of the particles or droplets. As a yet further example, particles or droplets to be investigated may be provided in varying sizes, and they all may be injected into the flow device simultaneously to investigate any measurable competition effect between the particles or droplets of different sizes on their respective activation and growth or shrinking behaviors.

As will be appreciated from the foregoing, the present invention offers a method and apparatus that accurately simulate the time dependence of drop growth or shrinking as it occurs, including in the lower atmosphere (troposphere). The method and apparatus permit accurate control of thermodynamic system parameters so as to establish a well-defined vapor concentration and saturation field. Further, the method and apparatus allow for observing the influence of trace gaseous species on droplet or particle growth or shrinking. Thus, the present invention offers a method and apparatus that are particularly useful for studying cloud droplet dynamic and microphysical processes.

EXAMPLE

An implementation of an apparatus for carrying out a method according to the present invention was modeled based on the calculations using the Computational Fluid Dynamics (CFD) code FLUENT together with a simple moving monodisperse droplet dynamical model. The calculations are based on a laminar flow device model, using the parameters and boundary conditions as listed in Table 1 below.

TABLE 1

| | |
|---|---|
| flow device length | 4 m |
| flow device radius | 3 cm |
| radius aerosol inlet | 0.5 cm |
| average velocity (aerosol inlet) | 0.1 m/s (Q ≈ 0.5 1/min) |
| average velocity (sheath air) | 0.1 m/s (Q ≈ 16.5 1/min)° |
| temperature (aerosol inlet) | 20° C. |
| temperature (sheath air) | 20° C. |
| temperature (wall) | 5° C. |
| relative humidity (aerosol inlet) | 96.6% |
| relative humidity (sheath air) | 96.6% |
| number concentration (aerosol inlet) | 100 cm$^{-3}$ |
| number concentration (sheath air) | 0 cm$^{-3}$ |
| seed particle diameter (dry) | 100 nm |
| seed particle material | NaCl |

Figure 4:
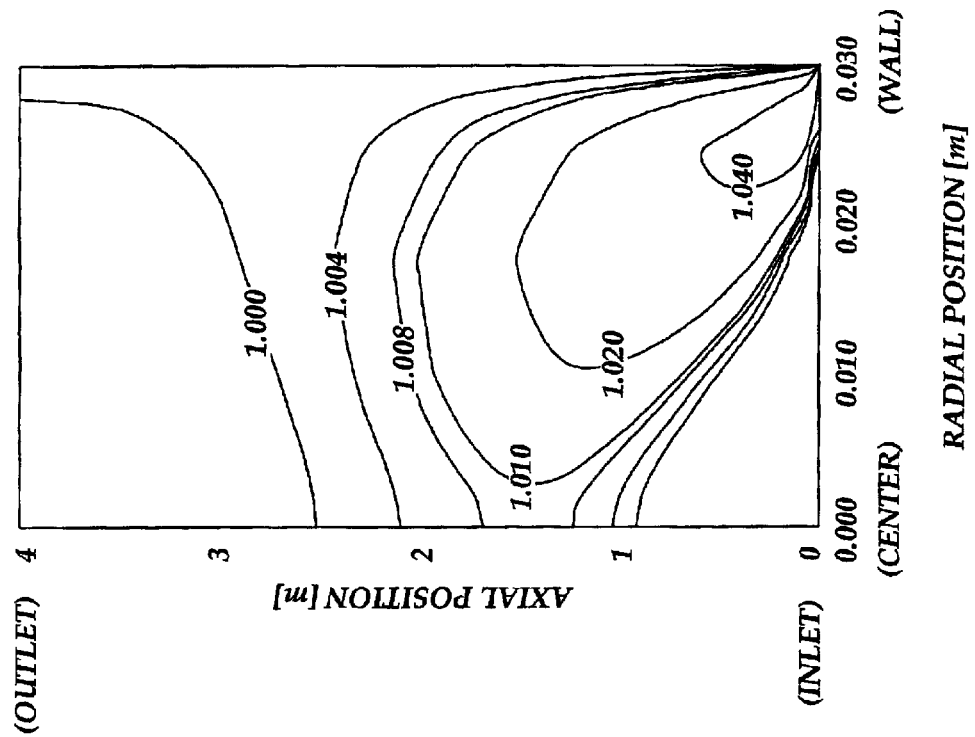
FIGS. 3–7 are graphs illustrating the performance of a flow device apparatus, calculated using the Computational Fluid Dynamics (CFD) code FLUENT.
Figure 3:
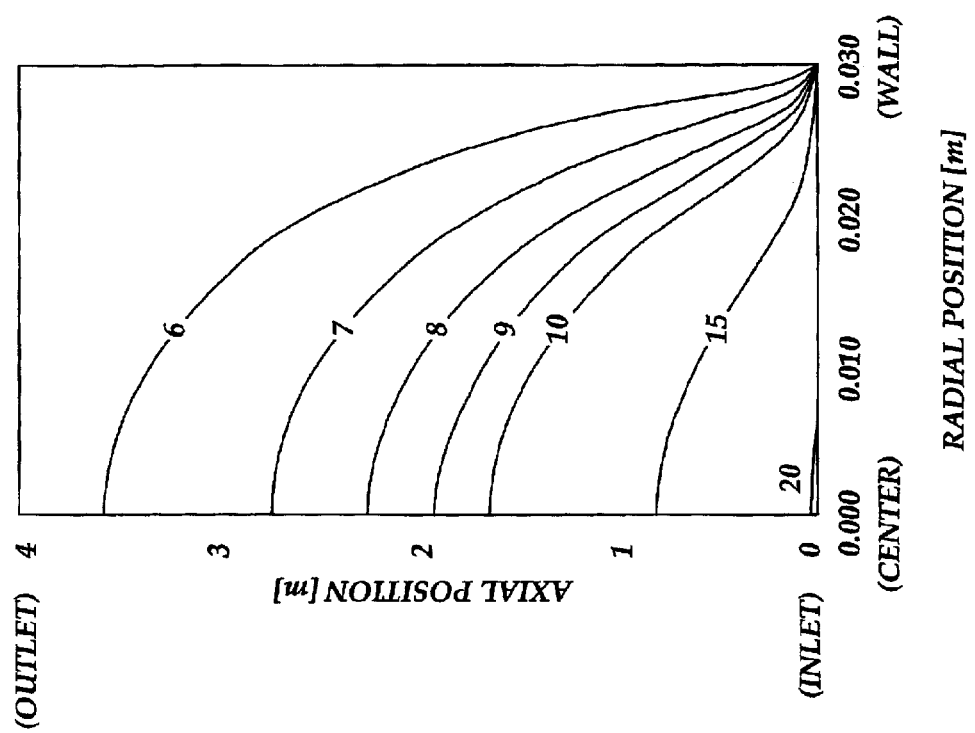

The "radius aerosol inlet" refers to the radius of an inlet through which aerosol (e.g., particles or droplets in a gas-vapor mixture to be investigated) enters the flow device. Referring additionally to FIGS. 3 and 4, temperature and saturation profiles, respectively, inside the flow device are illustrated (the flow direction is from bottom to top in FIGS. 3 and 4). As apparent from examining the saturation profile shown in FIG. 4, the water-air system in the flow device is inhomogeneous, with the maximum saturation reaching values larger than 1.04 near the device wall while the minimum saturation reaching values less than 1.01 near the device centerline. Assuming a homogeneous distribution of seed particles at the device inlet, the saturation field of FIG. 4 would yield a broad, maybe multi-modal droplet distribution, because the seed particles would experience a different saturation profile while traveling through the flow device depending on their radial position at the device inlet. This problem can be reduced by injecting seed particles only in a zone close to the device's radial centerline surrounded by particle-free sheath air. The radius of this injection zone (or the "aerosol inlet") should be chosen so as to minimize the radial inhomogeneities, i.e., as small as possible (e.g., in the order of millimeters).

Figure 5:
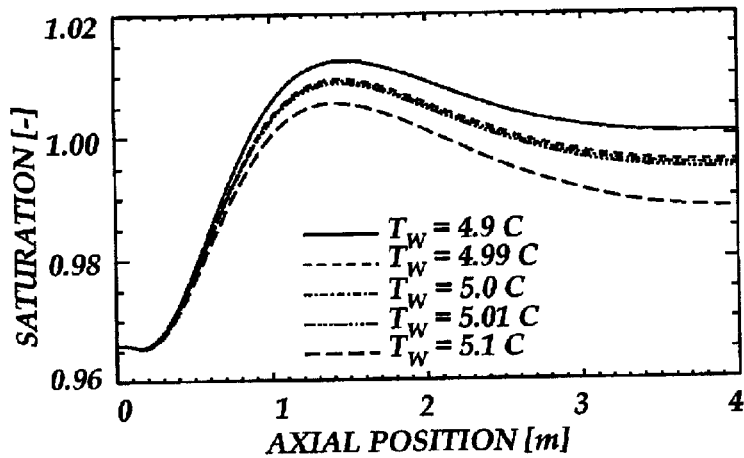
Figure 6:
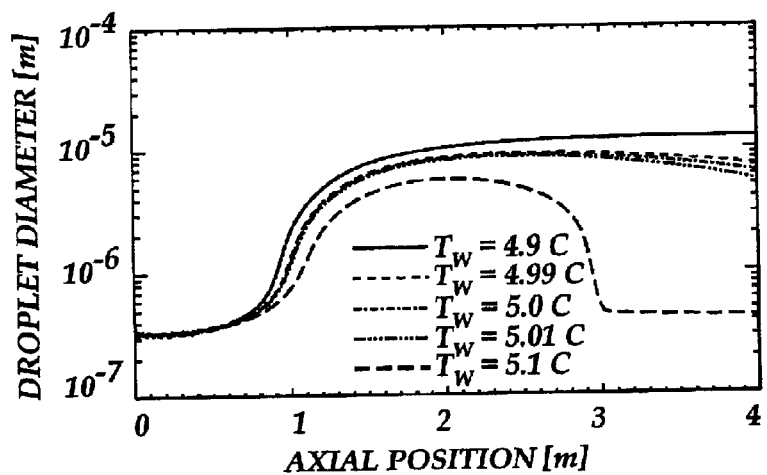

FIGS. 5 and 6 were prepared based on the assumption that the radius of the injection zone was 5 mm. FIG. 5 depicts saturation at the device centerline as a function of the axial position along the device and for different device wall temperatures ($T_W$=4.9, 4.99, 5.0, 5.01, 5.1° C.). FIG. 5 shows that saturation increases sharply approximately 0.3 m behind the inlet, reaches its maximum between 1 and 2 m, and then slowly decreases toward the outlet. Further, the dependence of saturation on the device wall temperature is illustrated. Wall temperatures of $T_W$=4.9, 4.99, 5.0, 5.01, and 5.1° C. result in maximum saturations of approximately 1.012, 1.0094, 1.0092, 1.0087, and 1.0055, respectively. FIG. 6 depicts the particle/droplet diameter at the device centerline as a function of the axial position along the device and for different device wall temperatures ($T_W$=4.9, 4.99, 5.0, 5.01, 5.1° C.). Comparing FIG. 6 against FIG. 5 will show that the droplet growth more or less follows the saturation profile. At a wall temperature of 5° C., the resulting droplet diameter exiting the flow device is about 6.3 micrometer. Increasing the wall temperature by 0.1° C. to 5.1° C. would result in the seed particles being activated but evaporating towards the outlet end of the flow device, while decreasing the wall temperature by 0.1° C. to 4.9° C. would produce droplets sized about 12 micrometer.

Figure 7:
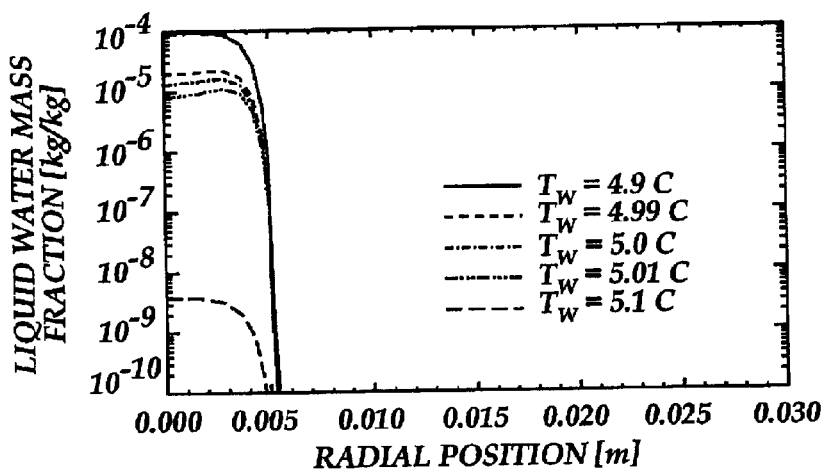

FIG. 7 depicts the liquid water mass fraction at the device outlet as a function of the radial position. Again, different temperatures are considered ($T_W$=4.9, 4.99, 5.0, 5.01, 5.1° C.). The liquid water mass fraction is nearly constant within the injection zone (radius≦5 mm) and drops sharply outside this zone. This indicates that particles/droplets experience similar supersaturation profiles while traveling through the flow device as long as they enter within the injection zone. FIG. 7 also shows the sensitivity of the system with respect to the wall temperature (more than 4 orders of magnitude difference in the liquid water mass ratio).

It should be understood that the above example was given merely to illustrate one particular application and its numerical results in accordance with the present invention, and is not intended to limit the scope of the invention. For example, the adoption of another growth model or different boundary conditions may change the numerical results significantly.

While the preferred embodiments of the invention have been illustrated and described, it will be appreciated that various changes can be made therein without departing from the spirit and scope of the invention.

The embodiments of the invention in which an exclusive property or privilege is claimed are defined as follows:

1. A method for investigating the behavior of particles or droplets in a gas-vapor mixture inside a flow device, comprising the steps of:
   (a) providing a flow device including an internal standard with known behavior;
   (b) after step (a), adjusting thermodynamic system parameters of the flow device based on observed behavior of the internal standard;

(c) after step (b), injecting particles or droplets to be investigated into the flow device;

(d) after step (c), measuring the size of the particles or droplets to be investigated; and (e) after step (d), determining the behavior of the particles or droplets to be investigated based on their measured size, the adjusted thermodynamic system parameters, and using a mathematical model.

2. The method of claim 1, further comprising, prior to step (c) of injecting particles or droplets to be investigated into the flow device, a step of removing the internal standard from the flow device.

3. The method of claim 1, wherein steps (c) through (e) are repeated by each time varying the thermodynamic system parameters.

4. The method of claim 1, wherein step (d) of measuring the size of the particles or droplets to be investigated comprises using space and/or time resolved measurements means.

5. The method of claim 4, wherein the space and/or time resolved measurements means comprise an optical measurement device.

6. The method of claim 1, wherein the flow device comprises a flow tube.

7. The method of claim 6, wherein the flow tube comprises a laminar flow tube.

8. The method of claim 1, wherein the internal standard comprises particles or droplets with known and/or determined size, chemical composition, concentration, and growth or shrinking behavior.

9. The method of claim 8, wherein the concentration of the particles or droplets is number concentration.

10. The method of claim 8, wherein a concentration profile of the particles or droplets forming the internal standard is predefined.

11. The method of claim 10, wherein the concentration profile is a number concentration profile.

12. The method of claim 1, wherein the thermodynamic system parameters are adjusted so as to achieve a desired particle or droplet size profile for the internal standard.

13. The method of claim 12, wherein step (b) of adjusting the thermodynamic system parameters further comprises:

determining a difference between a measured particle or droplet size and a desired particle or droplet size; and controlling the thermodynamic system parameters so as to minimize the difference.

14. The method of claim 13, wherein the particle or droplet size is measured along the axis of the flow device.

15. The method of claim 1, wherein the thermodynamic system parameters comprise boundary temperatures, vapor content, and pressure inside the flow device.

16. The method of claim 1, wherein the mathematical model comprises a mathematical/numerical model for determining fluid, thermodynamic, and chemical conditions in the flow device.

17. The method of claim 1, wherein the particles or droplets to be investigated have known and/or determined size and composition but have unknown growth or shrinking behavior, and the unknown growth or shrinking behavior of the particles or droplets is determined based on their measured size, the adjusted thermodynamic system parameters, and using a mathematical model.

18. The method of claim 1, wherein the particles or droplets to be investigated are injected into the flow device together with trace gasses, and effects of the trace gasses on the growth or shrinking behavior of the particles or droplets are determined.

19. The method according to claim 18, wherein trace gasses comprise gasses selected from the group consisting of $SO_2$, $NH_3$, and $HNO_3$.

20. The method of claim 1, wherein the particles or droplets to be investigated have known and/or determined concentration, and effects of the concentration on the activation and growth or shrinking behavior of the particles or droplets are determined.

21. The method of claim 1, wherein step (e) of determining the behavior of the particles or droplets to be investigated comprises determining a number of activated droplets.

22. The method of claim 1, wherein water droplets are investigated.

23. The method of claim 1, wherein the internal standard comprises sub-micrometer-sized NaCl particles.

24. The method of claim 1, wherein the thermodynamic system parameters are adjusted corresponding to the atmospheric cloud model so as to simulate thermodynamic conditions of real atmospheric clouds.

* * * * *